(12) United States Patent
Pfister

(10) Patent No.: US 11,013,481 B2
(45) Date of Patent: May 25, 2021

(54) METHOD FOR ACQUIRING AND PROCESSING IMAGE DATA OF AN EXAMINATION OBJECT

(71) Applicant: Marcus Pfister, Bubenreuth (DE)

(72) Inventor: Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 415 days.

(21) Appl. No.: 15/452,889

(22) Filed: Mar. 8, 2017

(65) Prior Publication Data

US 2017/0258430 A1 Sep. 14, 2017

(30) Foreign Application Priority Data

Mar. 9, 2016 (DE) .......................... 102016203857.5

(51) Int. Cl.
*A61B 6/00* (2006.01)
*G06T 7/11* (2017.01)
(Continued)

(52) U.S. Cl.
CPC ................ *A61B 6/504* (2013.01); *A61B 5/05* (2013.01); *A61B 5/489* (2013.01); *A61B 6/032* (2013.01);
(Continued)

(58) Field of Classification Search
CPC ........... A61B 5/05; A61B 5/055; A61B 5/489; A61B 6/032; A61B 6/4441; A61B 6/463;
(Continued)

(56) References Cited

U.S. PATENT DOCUMENTS

| 2005/0113679 A1 | 5/2005 | Suryanarayanan |
| 2006/0184006 A1 | 8/2006 | Chen |

(Continued)

FOREIGN PATENT DOCUMENTS

| CN | 1620990 A | 6/2005 |
| CN | 1307597 C | 3/2007 |

(Continued)

OTHER PUBLICATIONS

Fukuda, et al. (Evaluation of Automated 2D-3D Image Overlay System Utilizing Subtraction of Bone Marrow Image for EVAR: Feasibility Study, European Journal of Vascular and Endovascular Surgery vol. 46 Issue 1, 75-81 (2013) (Year: 2013).*

(Continued)

*Primary Examiner* — Joanne M Hoffman
*Assistant Examiner* — Alexei Bykhovski
(74) *Attorney, Agent, or Firm* — Lempia Summerfield Katz LLC

(57) ABSTRACT

A method for acquiring and processing image data of an examination object is provided. A three-dimensional bone model and a three-dimensional blood vessel model are provided. A two-dimensional, first X-ray image and a two-dimensional, second X-ray image of the examination region are acquired having a same image geometry. The first X-ray image is subtracted from the second X-ray image to provide a subtraction image. A first intermediate registration of the first X-ray image is determined in relation to the bone model, and a second intermediate registration of the subtraction image is determined in relation to the blood vessel model. A transformation function that images the first intermediate registration onto the second intermediate registration is determined. A third X-ray image of the examination region is acquired. A bone registration of the third X-ray image in relation to the bone model is determined.

18 Claims, 2 Drawing Sheets

(51) Int. Cl.

| | | |
|---|---|---|
| *G06T 7/00* | (2017.01) | |
| *G06T 7/38* | (2017.01) | |
| *A61B 5/05* | (2021.01) | |
| *A61B 6/03* | (2006.01) | |
| *A61B 5/00* | (2006.01) | |
| *G16H 50/50* | (2018.01) | |
| *G06T 7/33* | (2017.01) | |
| *A61B 5/055* | (2006.01) | |

(52) U.S. Cl.
CPC .............. *A61B 6/481* (2013.01); *A61B 6/487* (2013.01); *A61B 6/5205* (2013.01); *A61B 6/5235* (2013.01); *G06T 7/0012* (2013.01); *G06T 7/11* (2017.01); *G06T 7/33* (2017.01); *G06T 7/38* (2017.01); *G16H 50/50* (2018.01); *A61B 5/055* (2013.01); *A61B 6/4441* (2013.01); *A61B 6/463* (2013.01); *A61B 6/505* (2013.01); *G06T 2207/10016* (2013.01); *G06T 2207/10028* (2013.01); *G06T 2207/10081* (2013.01); *G06T 2207/10088* (2013.01); *G06T 2207/10116* (2013.01); *G06T 2207/20224* (2013.01); *G06T 2207/30008* (2013.01); *G06T 2207/30101* (2013.01)

(58) Field of Classification Search
CPC ......... A61B 6/481; A61B 6/487; A61B 6/504; A61B 6/505; A61B 6/5205; A61B 6/5235; G06T 2207/10016; G06T 2207/10028; G06T 2207/10081; G06T 2207/10088; G06T 2207/10116; G06T 2207/20224; G06T 2207/30008; G06T 2207/30101; G06T 7/0012; G06T 7/11; G06T 7/33; G06T 7/38; G16H 50/50
See application file for complete search history.

(56) References Cited

U.S. PATENT DOCUMENTS

| | | | |
|---|---|---|---|
| 2006/0262966 A1 | 11/2006 | Eck | |
| 2008/0275335 A1 | 11/2008 | Zhang | |
| 2012/0022366 A1 | 1/2012 | Pfister | |
| 2015/0141818 A1 | 5/2015 | Zhao | |
| 2016/0328855 A1* | 11/2016 | Lay ...................... | G06K 9/4614 |
| 2018/0040147 A1* | 2/2018 | Alhrishy ................. | A61B 6/02 |
| 2020/0051258 A1 | 2/2020 | Miao | |

FOREIGN PATENT DOCUMENTS

| | | |
|---|---|---|
| CN | 102342845 A | 2/2012 |
| CN | 103876764 A | 6/2014 |
| EP | 1510972 A2 | 3/2005 |
| WO | 2006063141 A2 | 6/2006 |

OTHER PUBLICATIONS

Wallace, et al. (Three-Dimensional C-arm Cone-beam CT: Applications in the Interventional Suite, J Vasc Interv Radiol 2008; 19: 799-813 (Year: 2008).*

Kauffmann, et al. (Source of Errors and Accuracy of a Two-Dimensional/Three-Dimensional Fusion Road Map for Endovascular Aneurysm Repair of Abdominal Aortic, JVIR, vol. 26, No. 4, pp. 544-551 (2015) (Year: 2015).*

Liao, et al. (Automatic and efficient contrast-based 2-D/3-D fusion for trans-catheter aortic valve implantation (TAVI), Computerized Medical Imaging and Graphics 37 (2013) 150-161 (Year: 2013).*

Dijkstra, et al. (Intraoperative C-arm cone-beam computed tomography in fenestrated/branched aortic endografting, the Society for Vascular Surgery, Journal of Vascular Surgery, vol. 53, No. 3, 583-589, Mar. 2011 (Year: 2011).*

Miao, et al. (Toward smart utilization of two X-ray images for 2-D/3-D registration applied to abdominal aortic aneurysm interventions, Computers and Electrical Engineering 39 (2013) 1485-1498) teaches accurate 2-D/3-D registration in 3-D space. (Year: 2013).*

Maintz et al (An Overview of Medical Image Registration Methods, Apr. 24, 2013—intelligence, 5:700-703, 1987). (Year: 1987).*

German Office Action for related German Application No. 10 2016 203 857.5 dated Dec. 22, 2016, with English Translation.

Kauffmann, C.: "Source of Errors and Accuracy of a Two-Dimensional/Three-Dimensional Fusion Road MapforEndovascularAneurysm Repair ofAbdominalAortic", in: JVIR, vol. 26, No. 4, pp. 544-551 (2015).

Miao, S. et. al.: "System and Method for 3-D/3-D Registration between Non-contrast-enhanced CBCT and Contrast-Enhanced CT for Abdominal Aortic Aneurysm Stenting", in: Medical Image Computing and Computer-Assisted Intervention—MICCAI 2013; vol. 8149 of the series Lecture Notes in Computer Science, pp. 380-387 (2013).

Miao, S. et. al.: "Toward smart utilization of two X-ray images for 2-D/3-D registration applied to abdominal aortic aneurysm interventions", in: Biomedical Engineering and Informations (BMEI) Shanghai, 2011, pp. 550-555.

Ponraj, C. et. al.: "3D-3D Image Fusion for EVAR Guidance: Comparison of Spine-Based vs Aortic Wall Calcification-Based Alignment", in: Journal of Vascular Surgery, vol. 61, No. 6S, pp. 139S-140S (2015).

Chinese Office Action for Chinese Application No. 201710130777.3 dated Jan. 6, 2020, with English translation.

Chinese Office Action for Chinese Application No. 201710130777.3 dated Sep. 10, 2020, with English translation.

* cited by examiner

METHOD FOR ACQUIRING AND PROCESSING IMAGE DATA OF AN EXAMINATION OBJECT

CROSS-REFERENCE TO RELATED APPLICATION

This application claims the benefit of DE 102016203857, filed on Mar. 9, 2016, which is hereby incorporated by reference in its entirety.

TECHNICAL FIELD

Embodiments relate to a method for acquiring and processing image data of an examination object and a medical image recording device.

BACKGROUND

Intra-operative imaging (e.g., via a C-arm X-ray unit) may be used during a large number of medical interventions in assisting an operator. An examination object is to remain accessible, however, so only limited imaging is possible. Exposure of an examination object to radiation and contrast medium may be reduced as far as possible. However, to be able to provide a maximum amount of information, 3D data sets may be acquired pre-operatively, 2D image data may be acquired inter-operatively, 3D data sets may be registered in relation thereto, and a corresponding representation of the 3D data set or an overlaying of a projection of the 3D data set may be displayed in relation to the 2D image data.

If, for example, an abdominal aortic aneurysm is to be treated by inserting a stent graft, the relevant part of the blood vessel system is visualized during the intervention. E-Example data from a CT angiography may be acquired pre-operatively and overlaid with X-ray or fluoroscopy images recorded during the treatment. For this kind of representation, the 2D and 3D data sets are registered with each other (e.g., transformed into a shared coordinate system).

When using contrast medium (e.g., free fluoroscopy images), the greatest contrasts may be caused by bones in the examination object. Registration of the data sets with respect to the bones may be sufficient at least for a first registration of the coordinate systems. The registration with respect to the bones may not be sufficient, however, for more accurate registration, for example of the vessels (aorta) with each other, since the position of the vessels in different data sets may be completely different due to patient positioning or introduction of instruments, etc. More accurate vessel registration may largely be achieved only by registration with angiographies that require administration (e.g., repeated administration) of contrast medium. To avoid repeated administration of the contrast medium, improved approaches that are based, for example, on a registration of the vessel system itself or on calcifications on the vessel system have been developed. A drawback is that the registration methods are typically relatively complex and linked with a C-arm CT, and may therefore only be carried out with difficulty during operation due to a C-arm rotation.

SUMMARY AND DESCRIPTION

Embodiments provide tracking of an existing registration of the vessels (e.g., aorta) without further administration of contrast medium, by intra-operative acquisition and processing of image data of the examination object, for example, in the course of fluoroscopy, in order to be able to compensate for patient movements.

In an embodiment, a method is provided for acquiring and processing image data of an examination object. A three-dimensional bone model that describes a bone structure in an examination region of an examination object is provided. A three-dimensional blood vessel model that describes a blood vessel system in the examination region is further provided. A two-dimensional, first X-ray image and a two-dimensional, second X-ray image of the examination region having the same image geometry for the first and second X-ray images are recorded. The first and second X-ray images are recorded at different concentrations of a contrast medium, which affects the contrast of the X-ray images, in the blood vessel system of the examination object. An item of disposition information that describes a disposition of the blood vessel system with respect to the bone structure is determined as a function of the first and second image recordings and the bone model and blood vessel model. A two-dimensional third X-ray image of the examination region is acquired. A bone registration of the bone model in relation to the third X-ray image is determined. A vessel registration of the blood vessel model in relation to the third image recording is determined as a function of the bone registration and disposition information.

In an embodiment, a first image recording and a second image recording of the examination region are acquired with different contrast medium concentrations. The acquisition of the image recordings is used, for example, in digital subtraction angiography. A subtraction image may be provided by subtraction of the first and second image recordings. The subtraction image depicts the regions having contrast change with administration of the contrast medium. The contrast medium may be supplied by the blood vessel system. The subtraction image primarily depicts the blood vessel system. The image recordings that were recorded with a lower concentration of contrast medium (e.g., with a concentration of close to zero) show the bones of the examination object. The image recording with a lower contrast medium concentration may be registered in relation to the bone model, and the subtraction image (or the contrast medium image) may be registered in relation to the blood vessel model. An item of disposition information that describes the different disposition of the blood vessel systems in the data sets with respect to the bone structure may be determined. The disposition information may describe, for example, the position of the bone model relative to the blood vessel model if the positions are both transformed into the coordinate system of the first and second image recordings. A registration of the blood vessel model may be derived for the same image recording from a registration of a bone model in relation to a two-dimensional image recording via the disposition information. After acquisition of the third image recording, the position of the vessel model with respect to the image recording may be determined with the aid of the disposition information even if the contrast of the image recording is influenced by bones (e.g., if no contrast medium is used in the course of the image recording).

A projection and/or a cross-section of the vessel model may be displayed as a function of the vessel registration. The projection or cross-section is displayed overlaid with the third image recording. Acquisition of third image recordings and determination of the representation of the vessel model as a function of the respective image recording and disposition information may be carried out repeatedly. Acquisition may occur, for example, in the course of a fluoroscopy in which a representation of image changes that is continuous for a viewer occurs due to high repetition rates of image recording.

The registrations may be rigid registrations or, for example an elastic registration. The concentrations of the contrast medium may be chosen such that the concentration in the first image recording is close to zero, and in the second image recording, a predefined concentration is attained in the blood vessel system.

In an embodiment, a three-dimensional image data set of the examination region to be segmented may provide the bone model and blood vessel model. The image data set may, for example, be acquired by a computer tomograph or a magnetic resonance tomograph. The three-dimensional image data set may be acquired by a further acquisition device that differs from the acquisition device by which the first and the second image recordings are recorded. For recording the first and second image recordings, an acquisition device may be used that provides access to the examination object, so access may be used effectively intra-operatively. The further acquisition device for acquiring the three-dimensional image data set may not enable good access to the examination object, as the three-dimensional image data set may be acquired pre-operatively.

The first, second, and third image recordings may be acquired as X-ray images by a single X-ray unit. The X-ray unit may be configured, for example, as a C-arm X-ray unit. X-ray units may enable relatively high-frequency imaging, so fluoroscopy (e.g., a continuous representation of X-ray images) may be provided. X-ray units may be configured to be relatively compact, enabling access to the examination object.

The third image recording may be recorded in the same image geometry as the first and second image recordings. In one embodiment, the third image recording may be recorded in a different image geometry. For example, a recording angle or a recording position may be changed.

Additionally, or alternatively, a first intermediate registration of the first image recording may be determined in relation to the bone model and a second intermediate registration of a subtraction image is calculated by subtraction of the first image recording from the second image recording that is determined in relation to the blood vessel model. A transformation function that images the first intermediate registration onto the second intermediate registration is determined as disposition information. The subtraction angiography may be used to determine a subtraction image that is dominated by the regions for which contrast changes as a function of the concentration of the contrast medium. The blood vessel system is imaged when contrast medium is administered via the blood vessel system. Simple and robust registration of the subtraction image in relation to the blood vessel model is possible. If a low concentration of contrast medium (e.g., no contrast medium) is used in the first image recording, then the first image recording is dominated by the bones of the examination object, whereby the first image recording may be easily and robustly registered in relation to the bone model. If a rigid registration is used, the transformation function may describe at least one translation and/or at least one rotation. If elastic registrations are used, different distortions (e.g., compressions or elongations and/or shearing) may be described by the transformation function.

The vessel registration may be determined by applying the transformation function to the bone registration. The transformation function images a 2D3D registration for the bone model onto a 2D3D registration for the blood vessel model. The bone registration is a registration between the bone model and the third image recording. By applying the transformation function, a vessel registration that registers the blood vessel model in relation to the third image recording results. For the third and for further subsequent image recordings, a registration is calculated in relation to the vessel model by a registration in relation to the bone system and applying the transformation function without further administration of contrast medium.

A representation of the vessel model is provided as a projection of the vessel model in the image plane of the third image recording, with a projection direction and/or a position and/or an orientation of the projection in the image plane and/or a distortion of the projection determined as a function of the third image recording and disposition information. The parameters of the projection may be determined as a function of the third image recording and the transformation function, for example as a function of the vessel registration. The projection may occur such that only boundary lines of the vessel model are displayed. Alternatively, a section of the vessel model may be displayed.

In an embodiment, a medical image recording device that has an acquisition device and a controller is provided. The acquisition device may be controlled to acquire a two-dimensional, first X-ray image and a two-dimensional, second X-ray image of an examination region of an examination object with the same image geometry for the first and second X-ray images. An item of disposition information that describes a disposition of the blood vessel system with respect to the bone structure may be determined as a function of the first and second image recordings. A three-dimensional bone model that describes a bone structure in the examination region may be provided. A three-dimensional blood vessel model that describes a blood vessel system in the examination region may be provided. The acquisition device may be controlled to acquire a third X-ray image of the examination region. A bone registration of the bone model may be determined in relation to the third X-ray image. A vessel registration of the vessel model may be determined in relation to the third image recording as a function of the bone registration and the disposition information.

The medical image recording device may be developed. The controller may provide requisite control functions for the acquisition device and/or a display device and may carry out the described procedures in the course of processing of the first and second image recordings as well as the bone model and blood vessel model.

Acquiring and processing image data of an examination object and/or the described medical image recording device or X-ray unit may be used for intra-operative imaging and visualization of the vessel system. Acquiring and processing image data may be used in the course of treatment of an abdominal aortic aneurysm by inserting a stent graft. Connection guide wires and catheters may be introduced into the aorta via the groin of the examination object, by which at least one stent graft (e.g., angioplasty) is introduced. For adequate fixing, the stent may be placed as deep as possible in the healthy vascular wall region but without covering important vessel exits. Exact visualization of the position of the aorta is provided.

Embodiments may be used for intra-operative imaging in the course of neuroradiology, abdominal interventional radiology and/or in the course of replacement of aortic valves.

Embodiments may provide a computer program and may be loaded, for example, directly into a storage device (e.g., a non-transitory computer-readable storage medium) of a controller of an image recording device, having program code (e.g., including instructions) to carry out the acts described herein when the program is run in the controller of the image recording device.

Embodiments provide an electronically readable data carrier including electronically readable control information stored thereon that includes a computer program product and is configured to carry out the acts described within when the data carrier is used in a controller of an image recording device.

The scope of the present invention is defined solely by the appended claims and is not affected to any degree by the statements within this summary. The present embodiments may obviate one or more of the drawbacks or limitations in the related art.

DETAILED DESCRIPTION

Figure 1:
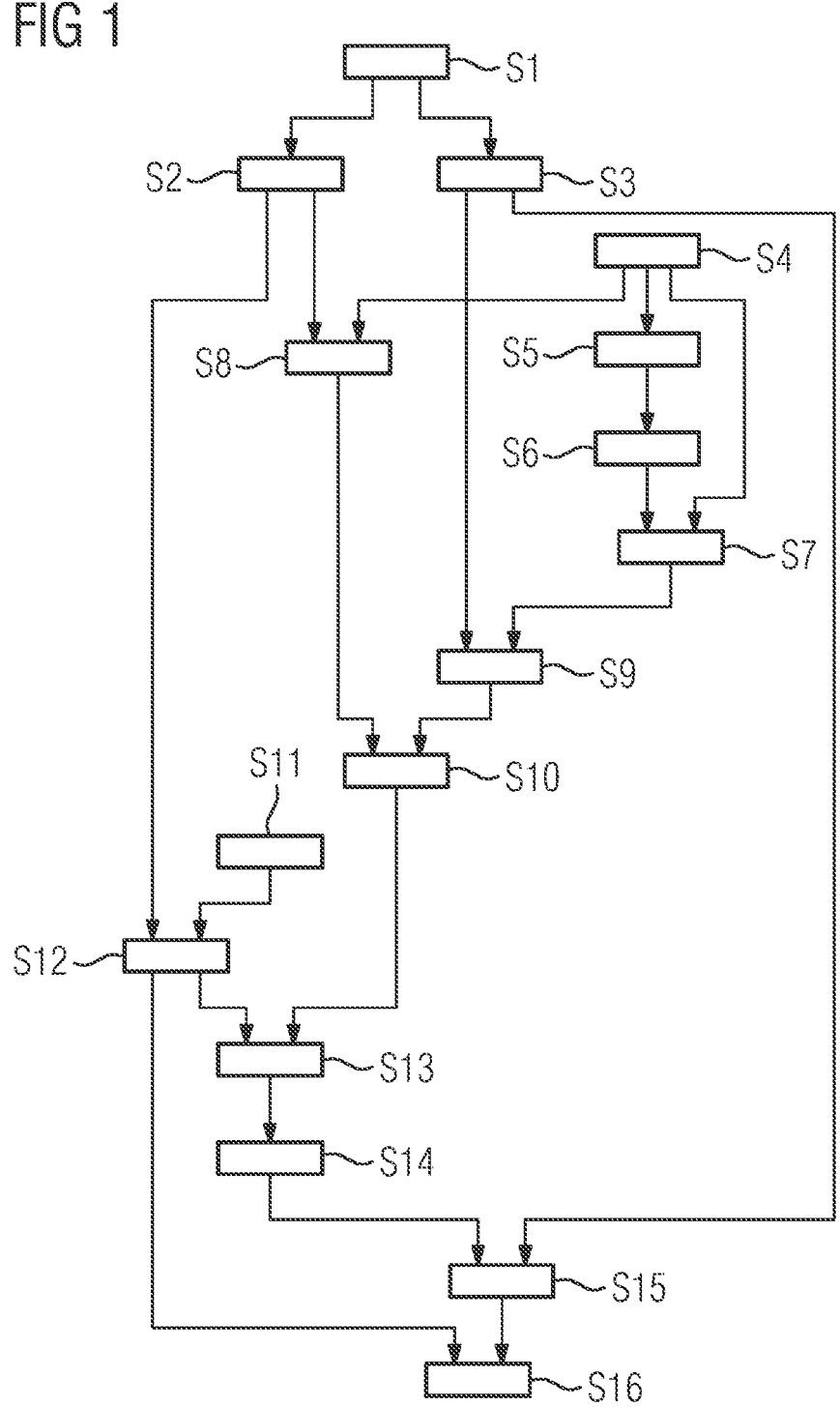
FIG. 1 depicts a flow diagram of an embodiment of a method.
Figure 2:
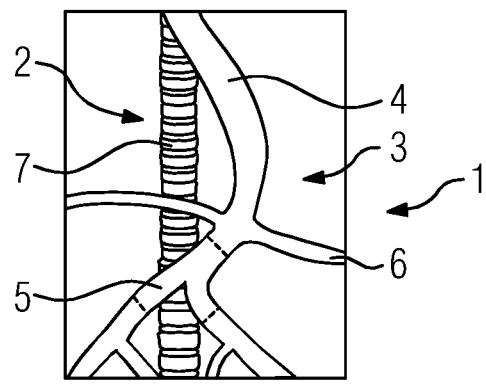
FIG. 2 depicts an example of an examination region where image data is to be acquired and processed.

FIG. 1 depicts an embodiment for acquiring and processing image data of an examination object that provides improved visualization of a blood vessel system, for example, in the case of intra-operative use. The embodiment is described with reference to FIG. 2 that depicts an examination region 1 that has image data to be acquired and processed. The bone structure 2 and the blood vessel system 3 are depicted in the examination region 1. The depicted examination region 1 may be visualized, for example, when treating an abdominal aortic aneurysm, i.e. an aneurysm of the abdominal aorta 4, to provide a physician with visual feedback when inserting a stent graft into the bifurcation region 5. The visualization may be used by a physician as the angioplasty may project as far as possible into the branches to make contact with healthy tissue, but without blocking exits of further vessels 6. Exact visual feedback is beneficial.

In the method depicted in FIG. 1 an X-ray image may periodically be acquired in the connection to provide a fluoroscopy. A projection of a blood vessel model may be overlaid on the X-ray image to improve detectability of the blood vessel system for a user. For this purpose, a three-dimensional image data set is recorded at act S1 by an acquisition device. For example, a CT angiography may be recorded by a computer tomograph. The three-dimensional image data set is segmented at acts S2 and S3, with a bone structure in the image data set segmented at act S2 to provide a three-dimensional bone model, and a blood vessel system being segmented at act S3 to provide a three-dimensional blood vessel model. Different methods may be used for segmentation of bone structures and/or blood systems in three-dimensional scan data.

Acts S1 to S3 may be carried out pre-operatively. A patient may then be positioned in a region in which, for example, image recording is done using a C-arm X-ray unit or another X-ray unit that provides good access to the patient, so that the subsequent imaging may occur intra-operatively. Following positioning of the patient, a two-dimensional, first X-ray image of the examination region 1 is recorded at act S4. A contrast medium is introduced into the blood vessel system 4 of the examination object at act S5. The contract medium influences the contrast of X-ray images. At act S6, a second X-ray image is recorded with the concentration of the contrast medium in the blood vessel system 3 being higher in the second X-ray image than in the first X-ray image. At act S7 the first X-ray image is subtracted from the second X-ray image, so that a subtraction image is provided that primarily visualizes the contrast changes in the regions with the concentration of the concentration agent. The subtraction image visualizes the blood vessel system 3.

At act S8 a first intermediate registration of the first X-ray image is determined in relation to the bone model. At act S9 a second intermediate registration of the subtraction image that was calculated at act S7, is determined in relation to the blood vessel model. A number of methods may be used for registration of two-dimensional image recordings in relation to three-dimensional image data sets. For example, features in the data sets may each be recognized and associated with each other and/or brightness- and/or gradient-based association methods may be used. For registration of the subtraction image in relation to the bone model, vertebrae 7, for example, are suitable as features that may be associated with each other. For registration of the blood vessel model in relation to the first X-ray image, bifurcations of the blood vessel system 3, for example, may be used as features.

By way of example, rigid registrations may be used. Rigid registrations may each describe up to three translations and up to three rotations that are used to transform the bone model or blood vessel model into a coordinate system based on the first X-ray image or the subtraction image, i.e. a coordinate system that is defined by the image geometry of the first and second X-ray images. Elastic registrations may be determined as the first and second intermediate registrations, in which additional registration parameters are determined that describe, for example, a compression, elongation and/or shearing of the bone model or blood vessel model for registration.

At act S10 a transformation function is determined that images the first intermediate registration onto the second intermediate registration. In the case of a rigid registration this transformation function corresponds to a series connection of up to three translations and up to three rotations in order to transform the coordinate systems described by the respective registrations into each other. With elastic registrations, corresponding compressions, elongations are provided to carry out the coordinate system transformation. Since the first and second intermediate registrations each represent a registration having two-dimensional image data, that is recorded in the same image geometry, the transformation function describes a function with which an X-ray image may be determined in relation to the bone model, an associated 2D-3D registration in relation to the blood vessel model from any 2D-3D registration.

At act S11 a third X-ray image of the examination region is acquired by the X-ray unit. The same image geometry may be used for the first and second X-ray images, although a different image geometry may also be used. For example, since recording of the first and second X-ray images, a recording angle of a C-arm X-ray unit may have been adjusted, the examination object may have moved or a table position of a patient table may have changed. The previously determined first and second intermediate registrations are not applicable to the third X-ray image in this case. At act S12 a bone registration of the third X-ray image is calculated in relation to the bone model. The third X-ray image may be recorded with a low concentration of contrast medium, for example zero, in the blood vessel system. The contrast in the X-ray image is dominated by the bone structure 2. Simple and robust registration in relation to the bone model may be used.

In an embodiment, the blood vessel model may be visualized. Repeated direct registration of an X-ray image, recorded with contrast medium, in relation to the blood vessel model may not be desirable in the course of fluoroscopy, however, and may be associated with stress for the patient. Since the bone model and the blood vessel model have been generated from a shared three-dimensional image data set, assuming that the position of the bones and vessels do not change relative to each other, the position of the blood vessel system may be determined in the coordinate system of the three-dimensional image data set in respect of the third X-ray image as a function of the position of the blood vessel model in respect of the bone model. This approach is defective, however, since the relative position of at least parts of the blood vessel system in relation to the bone structure may have changed between pre-operative recording of the three-dimensional image data set and intra-operative recording of the two-dimensional X-ray images. An embodiment uses the fact that a registration based on the bone model may be transformed by the transformation function into a registration based on the blood vessel model. The transformation function is applied at act S13 to the bone registration to obtain a vessel registration that describes a registration of the third X-ray image with the blood vessel model.

At act S14, projection parameters are calculated from the vessel registration. The projection parameters describe a projection of the blood vessel model in an image plane that corresponds to the image plane of the third X-ray image. The representation generated is overlaid at act S16 with the third X-ray image and displayed for the user by an output device of the X-ray unit. The image output may be updated periodically, or when an updating condition is fulfilled, by repeating the illustrated method from act S11.

The position of the blood vessel system may change intra-operatively in respect of the bone structure, for example when a patient has been repositioned, moves, instruments have been introduced into the vessel system, etc. With a user input, act S4 may be repeated periodically or when other conditions are fulfilled in order to re-determine the transformation function and the disposition information that describes a disposition of the blood vessel system in respect of the bone structure.

In an embodiment, the blood vessel system may be visualized repeatedly for a user or continuously in the course of fluorescence imaging, with an administration of contrast medium only used if an item of disposition information that describes the disposition of the blood vessel system in respect of the bone structure is to be updated. Compared with conventional visualization methods for intra-operative use, the frequency of an administration of contrast medium may therefore be significantly reduced, so stresses may be reduced for an examination object.

Figure 3:
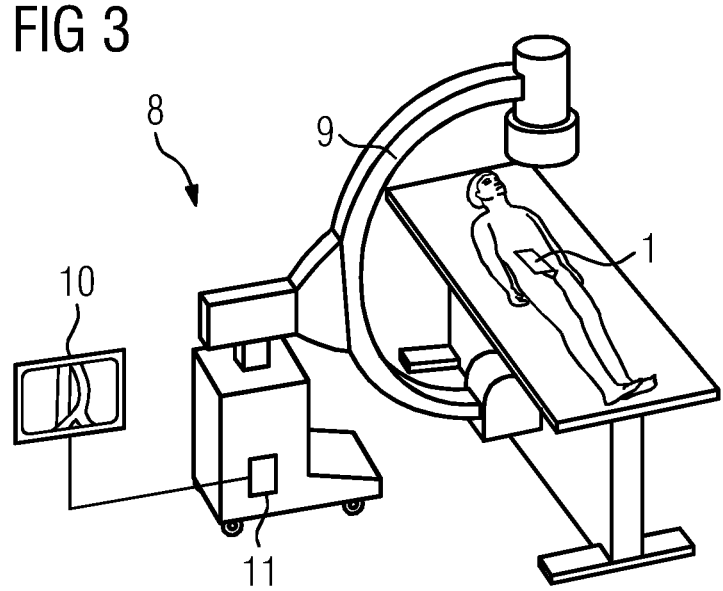
FIG. 3 depicts an embodiment of a medical image recording device.

FIG. 3 depicts a medical image recording device 8, for example, an X-ray unit, including an acquisition device 9 in the form of a C-arm, and a display device 10. The X-ray unit is configured to carry out the acts S4-16 of the workflow depicted in FIG. 1, apart from the administration of contrast medium in act S5. The X-ray unit includes a controller 11 configured to control the acquisition device 9 for acquiring the first, second and third X-ray images. The controller may subtract X-ray images to provide a subtraction image and determine the first and second intermediate registrations and the bone registration. Furthermore, the transformation function may be determined using the controller 11 as described above, and a vessel registration may be determined with the aid of the transformation function. With the transformation function, the blood vessel model may be projected into an image plane of the third X-ray image. The controller 11 may overlay the projection with the third X-ray image and the display device 10 may display the overlaying.

In an embodiment, a computer program product may implement the workflow on a controller 11 when the computer program is run on the controller 11. An electronically readable data carrier (not shown) may be included, the data carrier having electronically readable control information stored thereon that includes at least one described computer program product and is configured in such a way that the computer program product carries out a described workflow when the data carrier is used in a controller 11 of an image recording device 8.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquiring and processing image data of an examination object, the method comprising:
providing a three-dimensional image data set of an examination region of the examination object;
segmenting the three-dimensional image data set to provide a three-dimensional bone model that describes a bone structure in the examination region of the examination object;
acquiring, by an X-ray unit, a two-dimensional, first X-ray image of the examination region without a contrast medium;
registering the first X-ray image with the three-dimensional bone model to provide a first intermediate registration;
segmenting the three-dimensional image data set to provide a three-dimensional blood vessel model that describes a blood vessel system in the examination region, wherein the three-dimensional blood vessel model is separate from and does not include the three-dimensional bone model;
injecting the contrast medium into the blood vessel system of the examination region;
acquiring, by the X-ray unit, a two-dimensional, second X-ray image of the examination region, wherein the first X-ray image and the second X-ray image have a same image geometry, and wherein the second X-ray image is acquired with a higher concentration of the contrast medium in the blood vessel system than the first X-ray image;

generating a subtraction image, the generating of the subtraction image comprising subtracting the first X-ray image from the second X-ray image;

registering the subtraction image with the three-dimensional blood vessel model to provide a second intermediate registration;

determining a transformation function that maps the first intermediate registration onto the second intermediate registration, wherein: (1) the first and second intermediate registrations are rigid registrations, and the transformation function corresponds to a series connection of one to three translations and one to three rotations to transform coordinate systems described by the first and second intermediate registrations; or (2) the first and second intermediate registrations are elastic registrations, and corresponding compressions and/or elongations are provided to determine the transformation function;

acquiring, by the X-ray unit, a third X-ray image of the examination region;

determining a bone registration of the third X-ray image using the three-dimensional bone model segmented from the three-dimensional image data set; and determining a vessel registration of the third X-ray image by applying the transformation function to the bone registration of the third X-ray image.

2. The method of claim 1, wherein the providing of the three-dimensional image data set comprises:

acquiring, by an image recording device, the three-dimensional image data set that images the examination region of the examination object.

3. The method of claim 1, further comprising:

displaying, by a display, a representation of the three-dimensional blood vessel model overlaid with the third X-ray image.

4. The method of claim 3, wherein the representation of the three-dimensional blood vessel model is a projection of the three-dimensional blood vessel model in an image plane of the third X-ray image, and wherein a projection direction, a position, an orientation, or any combination thereof of the projection in the image plane, a distortion of the projection, or a combination thereof is determined as a function of the vessel registration.

5. The method of claim 2, wherein the image recording device comprises a computer tomograph or a magnetic resonance tomograph.

6. The method of claim 1, wherein the X-ray unit comprises a C-arm X-ray unit.

7. An X-ray unit comprising:

an acquisition device configured to acquire a two-dimensional, first X-ray image of an examination region of an examination object without a contrast medium, acquire a two-dimensional, second X-ray image of the examination region with the contrast medium, and acquire a third X-ray image of the examination region, wherein the first X-ray image and the second X-ray image have a same image geometry; and a controller configured to:

receive a three-dimensional bone model that describes a bone structure in the examination region of the examination object, wherein the three-dimensional bone model has been segmented from a three-dimensional image data set;

register the first X-ray image with the three-dimensional bone model to provide a first intermediate registration;

receive a three-dimensional blood vessel model that describes a blood vessel structure in the examination region of the examination object, wherein the three-dimensional blood vessel model has been segmented from the three-dimensional image data set, and wherein the three-dimensional blood vessel model is separate from and does not include the three-dimensional bone model;

subtract the first X-ray image from the second X-ray image to provide a subtraction image;

register the subtraction image with the three-dimensional blood vessel model to provide a second intermediate registration;

determine a transformation function that maps the first intermediate registration onto the second intermediate registration, wherein: (1) the first and second intermediate registrations are rigid registrations, and the transformation function corresponds to a series connection of one to three translations and one to three rotations to transform coordinate systems described by the first and second intermediate registrations; or (2) the first and second intermediate registrations are elastic registrations, and corresponding compressions and/or elongations are provided to determine the transformation function;

determine a bone registration of the third X-ray image using the three-dimensional bone model segmented from the three-dimensional image data set; and determine a vessel registration of the third X-ray image by applying the transformation function to the bone registration of the third X-ray image.

8. A computer program product comprising:

a non-transitory computer-readable storage medium storing instructions executable by a controller of an image recording device to acquire and process image data of an examination object, the instructions, when executed, cause the controller to:

receive a three-dimensional image data set of an examination region of the examination object;

segment the three-dimensional image data set to provide a three-dimensional bone model that describes a bone structure in the examination region of the examination object;

acquire, by an X-ray unit, a two-dimensional, first X-ray image of the examination region without a contrast medium;

register the first X-ray image with the three-dimensional bone model to provide a first intermediate registration;

segment the three-dimensional image data set to provide a three-dimensional blood vessel model that describes a blood vessel system in the examination region, wherein the three-dimensional blood vessel model is separate from and does not include the three-dimensional bone model;

acquire, by the X-ray unit, a two-dimensional, second X-ray image of the examination region, wherein the first X-ray image and the second X-ray image have a same image geometry, and wherein the second X-ray image is acquired with a higher concentration of the contrast medium in the blood vessel system than the first X-ray image;

generate a subtraction image by subtracting the first X-ray image from the second X-ray image;

register the subtraction image with the three-dimensional blood vessel model to provide a second intermediate registration;

determine a transformation function that maps the first intermediate registration onto the second intermediate registration wherein: (1) the first and second intermediate registrations are rigid registrations, and the transformation function corresponds to a series connection of one to three translations and one to three rotations to transform coordinate systems described by the first and second intermediate registrations; or (2) the first and second intermediate registrations are elastic registrations, and corresponding compressions and/or elongations are provided to determine the transformation function;

acquire, by the X-ray unit, a third X-ray image of the examination region;

determine a bone registration of the third X-ray image using the bone model segmented from the three-dimensional image data set; and determine a vessel registration of the third X-ray image by applying the transformation function to the bone registration of the third X-ray image.

9. A non-transitory computer-readable storage medium storing instructions executable by a controller of an image recording device to acquire and process image data of an examination object, the instructions, when executed, cause the controller to:

receive a three-dimensional image data set of an examination region of the examination object;

segment the three-dimensional image data set to provide a three-dimensional bone model that describes a bone structure in the examination region of the examination object;

acquire, by an X-ray unit, a two-dimensional, first X-ray image of the examination region without a contrast medium;

register the first X-ray image with the three-dimensional bone model to provide a first intermediate registration;

segment the three-dimensional image data set to provide a three-dimensional blood vessel model that describes a blood vessel system in the examination region, wherein the three-dimensional blood vessel model is separate from and does not include the three-dimensional bone model;

acquire, by the X-ray unit, a two-dimensional, second X-ray image of the examination region, wherein the first X-ray image and the second X-ray image have a same image geometry, and wherein the second X-ray image is acquired with a higher concentration of the contrast medium in the blood vessel system than the first X-ray image;

generate a subtraction image by subtracting the first X-ray image from the second X-ray image;

register the subtraction image with the three-dimensional blood vessel model to provide a second intermediate registration;

determine a transformation function that maps the first intermediate registration onto the second intermediate registration wherein: (1) the first and second intermediate registrations are rigid registrations, and the transformation function corresponds to a series connection of one to three translations and one to three rotations to transform coordinate systems described by the first and second intermediate registrations; or (2) the first and second intermediate registrations are elastic registrations, and corresponding compressions and/or elongations are provided to determine the transformation function;

acquire, by the X-ray unit, a third X-ray image of the examination region;

determine a bone registration of the third X-ray image using the bone model segmented from the three-dimensional image data set; and determine a vessel registration of the third X-ray image by applying the transformation function to the bone registration of the third X-ray image.

10. The non-transitory computer-readable storage medium of claim 9, wherein the receipt of the three-dimensional bone model comprises acquisition, by the image recording device, of the three-dimensional image data set that images the examination region of the examination object.

11. The non-transitory computer-readable storage medium of claim 9, wherein the instructions, when executed, further cause the controller to:

display, by a display, a representation of the three-dimensional blood vessel model overlaid with the third X-ray image.

12. The non-transitory computer-readable storage medium of claim 11, wherein the representation of the three-dimensional blood vessel model is a projection of the three-dimensional blood vessel model in an image plane of the third X-ray image, and wherein a projection direction, a position, an orientation, or any combination thereof of the projection in the image plane, a distortion of the projection, or a combination thereof is determined as a function of the vessel registration.

13. The non-transitory computer-readable storage medium of claim 10, wherein the image recording device comprises a computer tomograph or a magnetic resonance tomograph.

14. The non-transitory computer-readable storage medium of claim 9, wherein the X-ray unit comprises a C-arm X-ray unit.

15. The method of claim 1, wherein the third X-ray image of the examination region is acquired with a concentration of zero of the contrast medium in the examination region.

16. The method of claim 1, wherein the first and second intermediate registrations are the rigid registrations.

17. The method of claim 1, wherein the first and second intermediate registrations are the elastic registrations.

18. The method of claim 1, wherein the determining of the vessel registration of the third X-ray image is performed even when the contrast medium in the acquiring of the third X-ray image is influenced by the bone structure of the examination object.

* * * * *